United States Patent
Abu-Omar et al.

(10) Patent No.: US 10,793,482 B2
(45) Date of Patent: Oct. 6, 2020

(54) COMPOUNDS AND COMPOSITIONS FOR DELIVERY OF NUTRIENTS AND MICRONUTRIENTS TO PLANTS

(71) Applicant: Spero Energy, Inc., Thousand Oaks, CA (US)

(72) Inventors: Mahdi M. Abu-Omar, Goleta, CA (US); Basudeb Saha, West Lafayette, IN (US); Ian Klein, Ventura, CA (US)

(73) Assignee: Spero Energy, Inc., Goleta, CA (US)

(*) Notice: Subject to any disclaimer, the term of this patent is extended or adjusted under 35 U.S.C. 154(b) by 274 days.

(21) Appl. No.: 15/740,326

(22) PCT Filed: Jun. 28, 2016

(86) PCT No.: PCT/US2016/039837
§ 371 (c)(1),
(2) Date: Dec. 27, 2017

(87) PCT Pub. No.: WO2017/004052
PCT Pub. Date: Jan. 5, 2017

(65) Prior Publication Data
US 2018/0208514 A1    Jul. 26, 2018

Related U.S. Application Data

(60) Provisional application No. 62/186,206, filed on Jun. 29, 2015.

(51) Int. Cl.
- C05D 9/00 (2006.01)
- C05D 9/02 (2006.01)
- C07C 229/14 (2006.01)
- C07C 229/24 (2006.01)
- C07C 229/38 (2006.01)
- A61K 31/195 (2006.01)
- C05C 9/00 (2006.01)

(52) U.S. Cl.
CPC .............. C05D 9/02 (2013.01); A61K 31/195 (2013.01); C05C 9/00 (2013.01); C07C 229/14 (2013.01); C07C 229/24 (2013.01); C07C 229/38 (2013.01)

(58) Field of Classification Search
None
See application file for complete search history.

(56) References Cited

U.S. PATENT DOCUMENTS 3,132,934 A    5/1964   Richard et al.
4,018,799 A *  4/1977   Scott .................... C07C 255/00
                                                          549/399

(Continued)

OTHER PUBLICATIONS

M. Thirumavalavan et al, "Synthesis and characterization of u-phenoxo-bridged binuclear coipper (II) complexes derived from binucleating ligands", Indian Journal of Chemical Technology (2004), 11 (1), 29-34.*

(Continued)

Primary Examiner — Wayne A Langel
(74) Attorney, Agent, or Firm — Ice Miller LLP

(57) ABSTRACT

Compounds, including chelated compounds, which may be used for the delivery of nutrients and micronutrients to plants are provided. In addition, processes for preparing such compounds, compositions comprising such compounds, and methods for delivering nutrients and micronutrients to plants with such compounds are provided.

29 Claims, 15 Drawing Sheets

2-methoxy-4-propylphenol (dihydroeugenol, DHE) based chelates

DHE-IA: R = H
DHE-IMA: R = Me
DHE-IDA: R = -CH$_2$COOH

(56) References Cited

U.S. PATENT DOCUMENTS

| | | | |
|---|---|---|---|
| 6,333,292 B1 | 12/2001 | Gibson et al. | |
| 6,436,152 B1 * | 8/2002 | Chassot | A61K 8/411 |
| | | | 8/405 |
| 2003/0070241 A1 * | 4/2003 | Chassot | A61K 8/411 |
| | | | 8/405 |
| 2008/0254498 A1 * | 10/2008 | Diwu | C07C 229/24 |
| | | | 435/29 |
| 2010/0168469 A1 * | 7/2010 | Nawrocki | C07C 249/02 |
| | | | 562/448 |

OTHER PUBLICATIONS

"Pubchem CID 20715009" Create Date: Dec. 5, 2007 (Dec. 5, 2007) Date Accessed: Nov. 17, 2016 (Nov. 17, 2016); p. 4, compound listed.

* cited by examiner

Figure 1. 2-methoxy-4-propylphenol (dihydroeugenol, DHE) based chelates
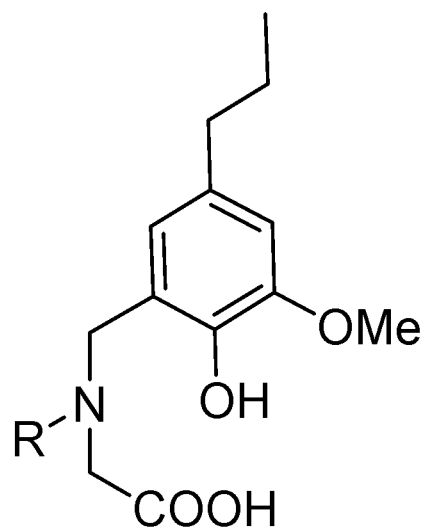
DHE-IA: R = H
DHE-IMA: R = Me
DHE-IDA: R = -CH$_2$COOH Figure 2. Propylsyringol, DMPP-derivatives, MPC (methoxypropyl catechol) and PTP (propyl triphenol).
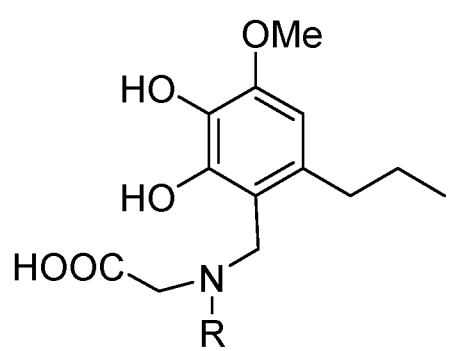
MPC-IA: R = H
MPC-IMA: R = Me
MPC-IDA: R = -CH$_2$COOH
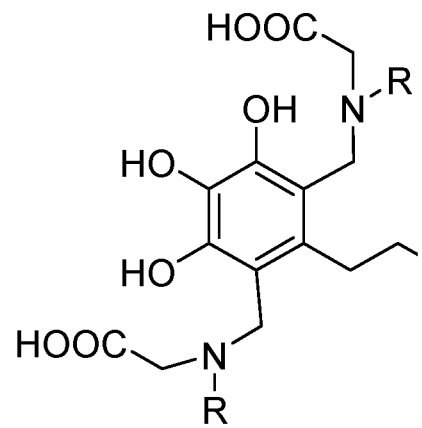
PTP-IA: R = H
PTP-IMA: R = Me
PTP-IDA: R = -CH$_2$COOH Figure 3. DHE-derivatives and *o*-hydroxyphenol chelates (OHP).
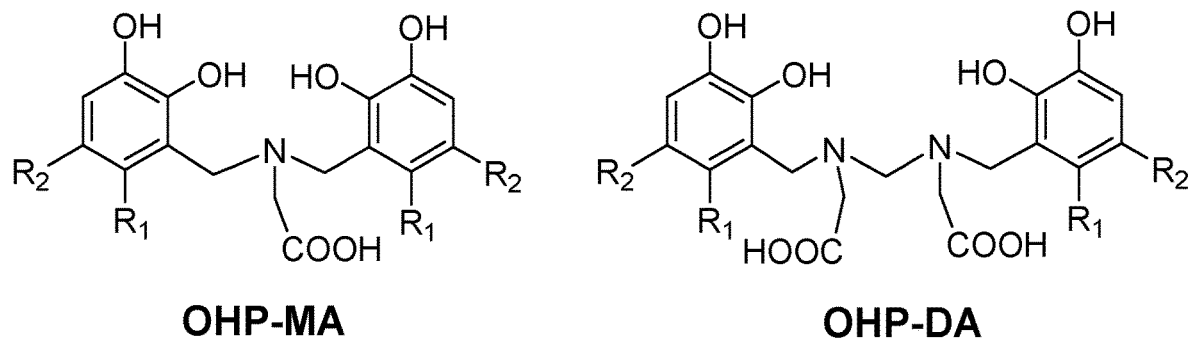
$R_1$ = H, $R_2$ = H
$R_1$ = H, $R_2$ = Me, Et, or $^n$Pr
$R_1$ = Me or Et, $R_2$ = Me or Et

Figure 4. Phenol based imino acid chelates.
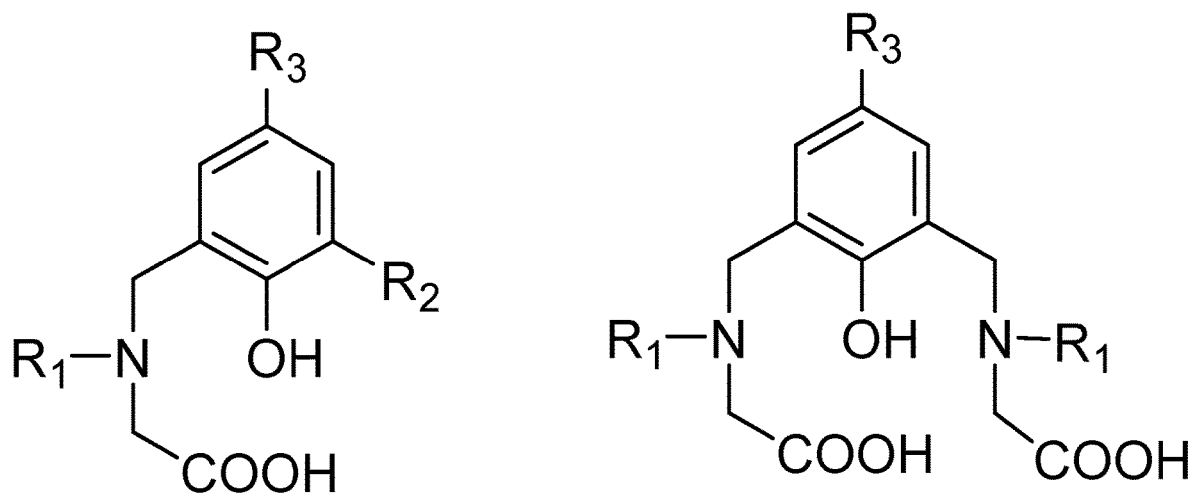
$R_1$ = H, Me, or -CH$_2$COOH
$R_2$ = Me, OMe, Et, OEt, Pr, or $^t$Bu
$R_3$ = Me, OMe, Et, OEt, Pr, or $^t$Bu

Figure 5. Para-substituted phenol (PP) chelates
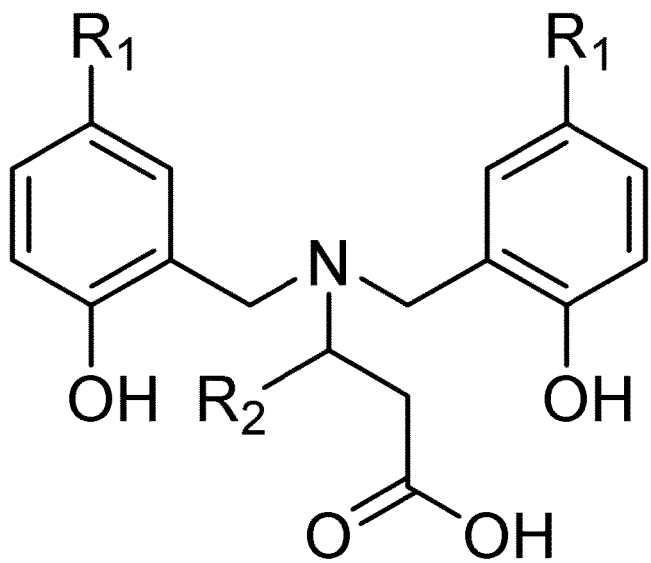
where $R_1$ is $SO_3M$, COOM, or a $C_1$-$C_4$ alkyl; $R_2$ is $CH_2COOH$, $CH_2OH$, $CHOHCH_3$, $CH_2SH$, $CH_2CH_2COOH$, or $CH_2CH_2SCH_3$; and M is an alkali metal.

Figure 6. PP Structures
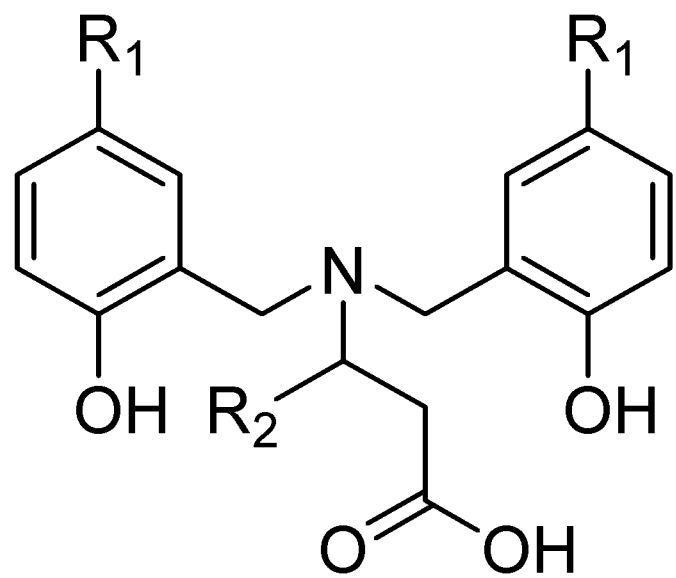
PP-Sulf-Asp: $R_1 = SO_3M$, $R_2 = CH_2COOH$, M = an alkali metal
PP-Cres-Asp: $R_1 = CH_3$, $R_2 = CH_2COOH$ Figure 7. ¹H-NMR spectrum of DHE-IMA crude product obtained from a reaction described in Example 1.
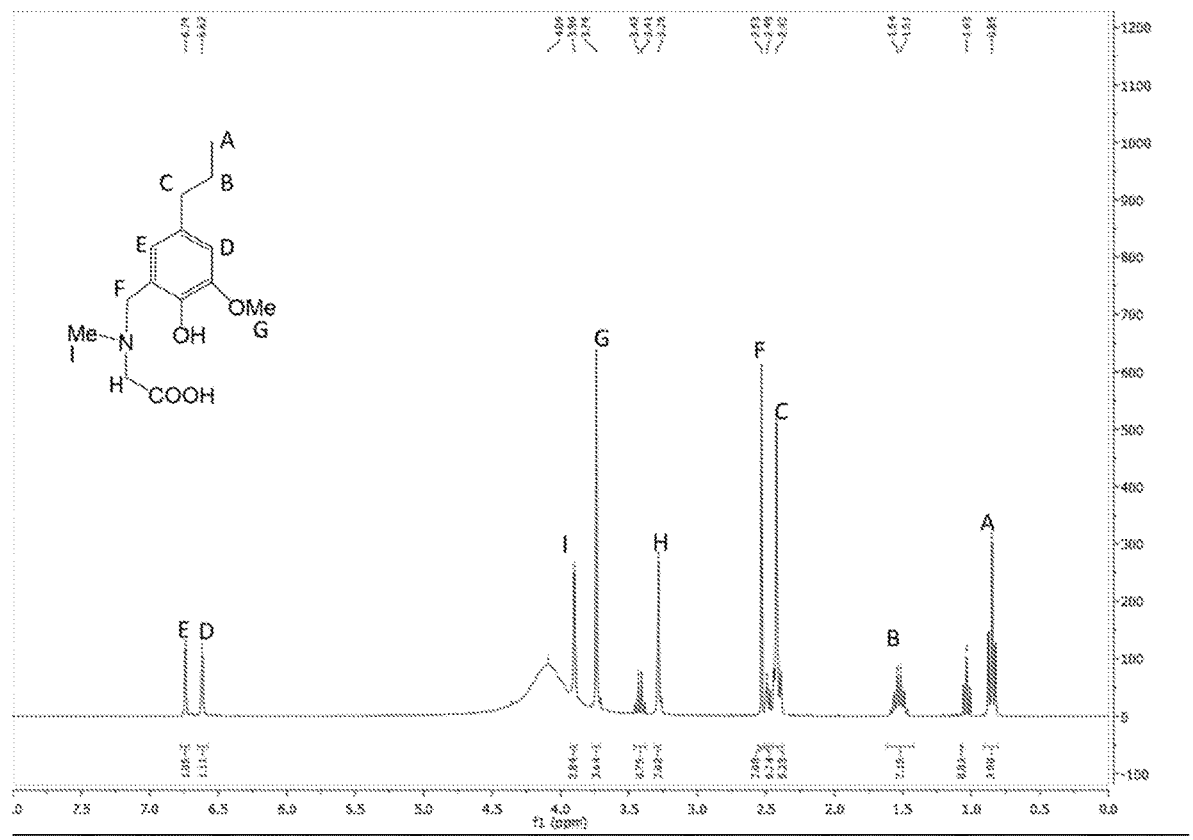

Figure 8. $^1$H-NMR of DHE-IDA obtained from a reaction described in Example 2.
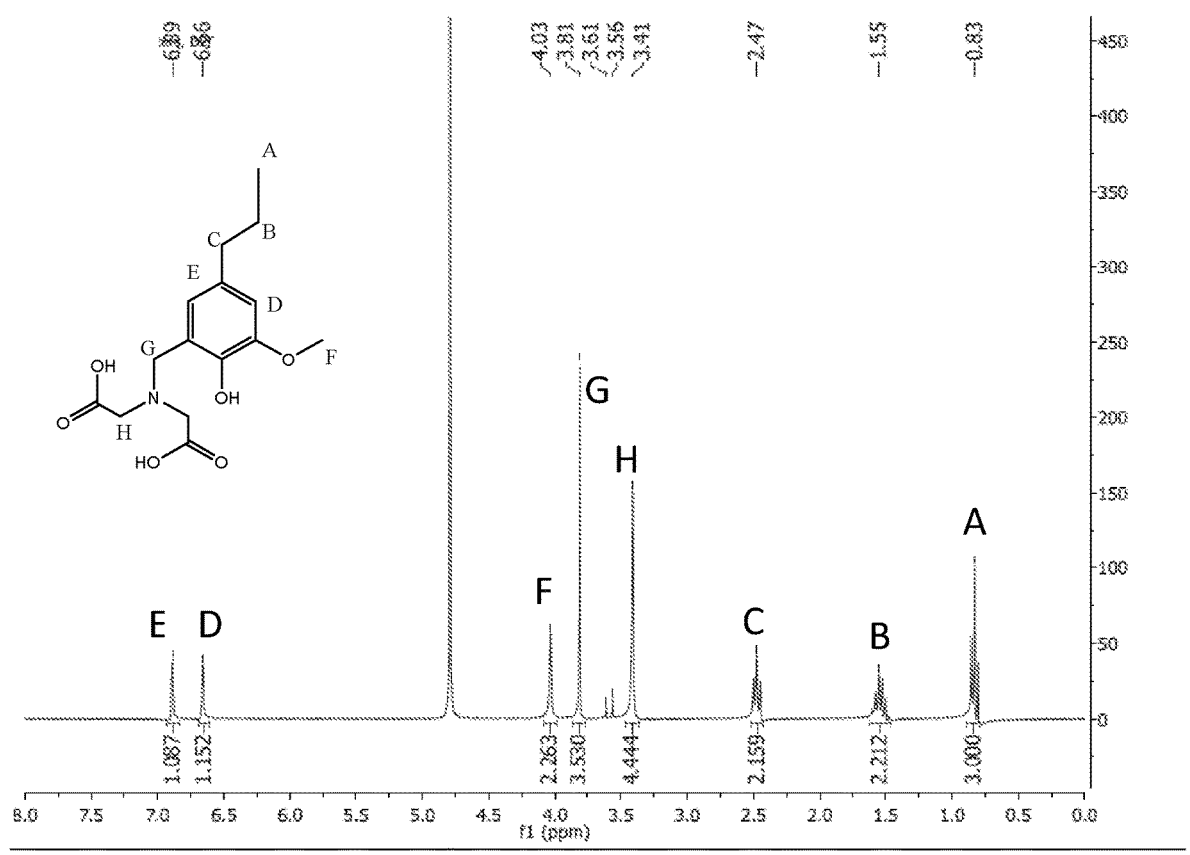

Figure 9. $^1$H-NMR spectrum of Cres-IMA obtained from a reaction described in Example 3.
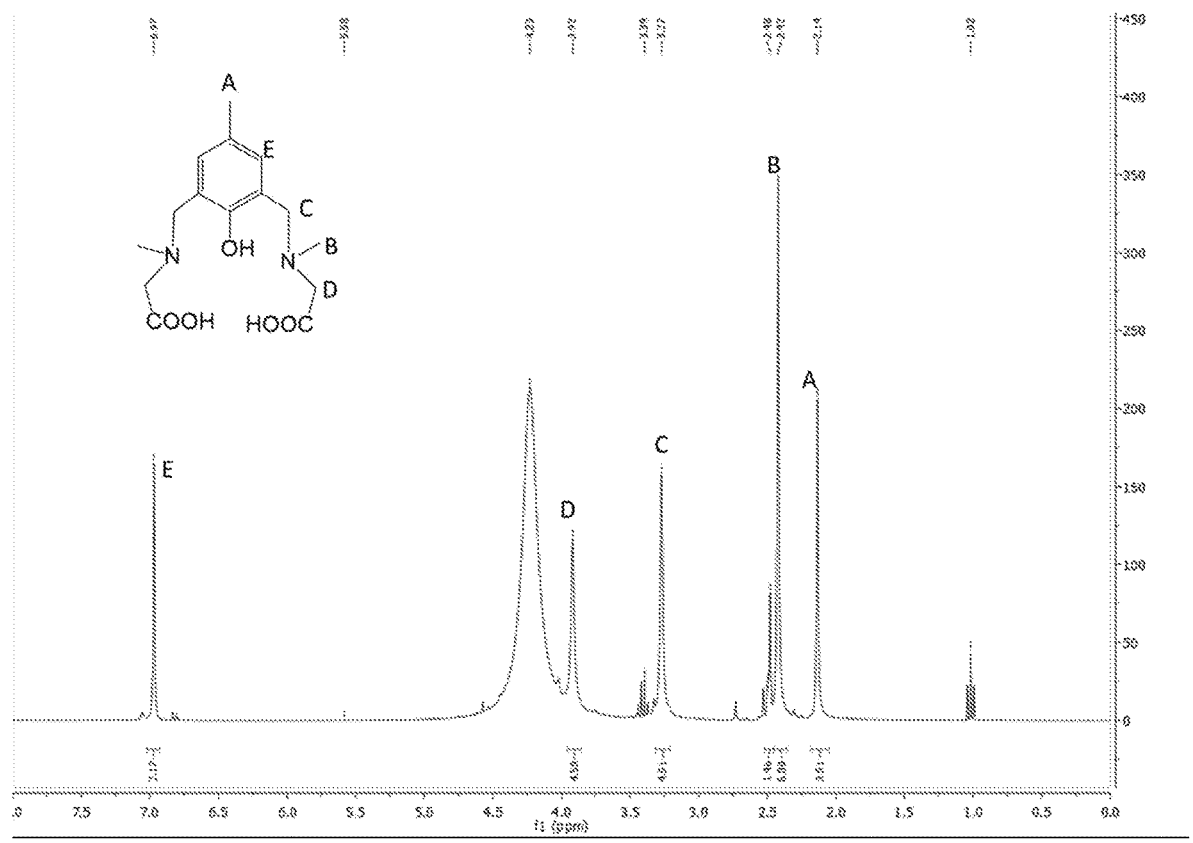

Figure 10. $^1$H-NMR of Cres-IDA obtained from a reaction described in Example 4.
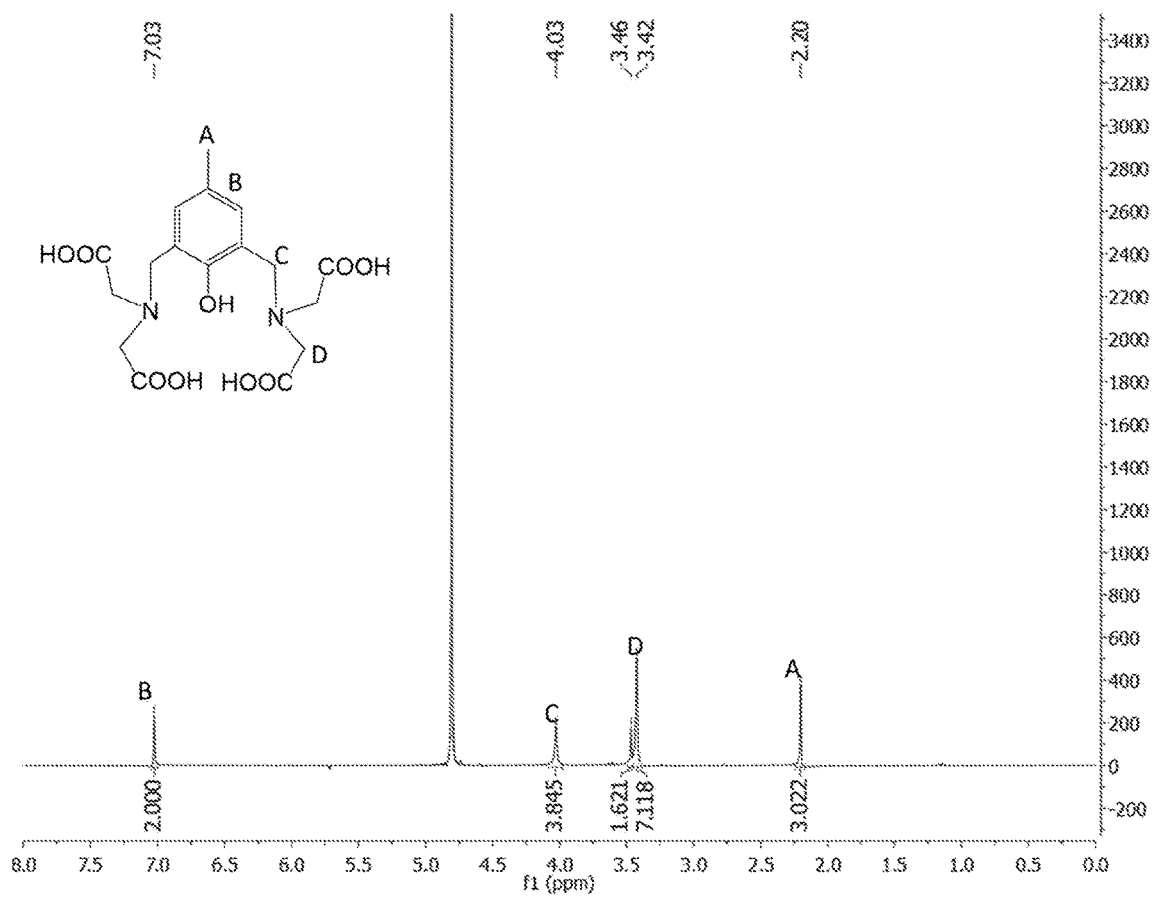

Figure 11. $^1$H-NMR of Me$_2$P-IMA obtained from a reaction described in Example 6.
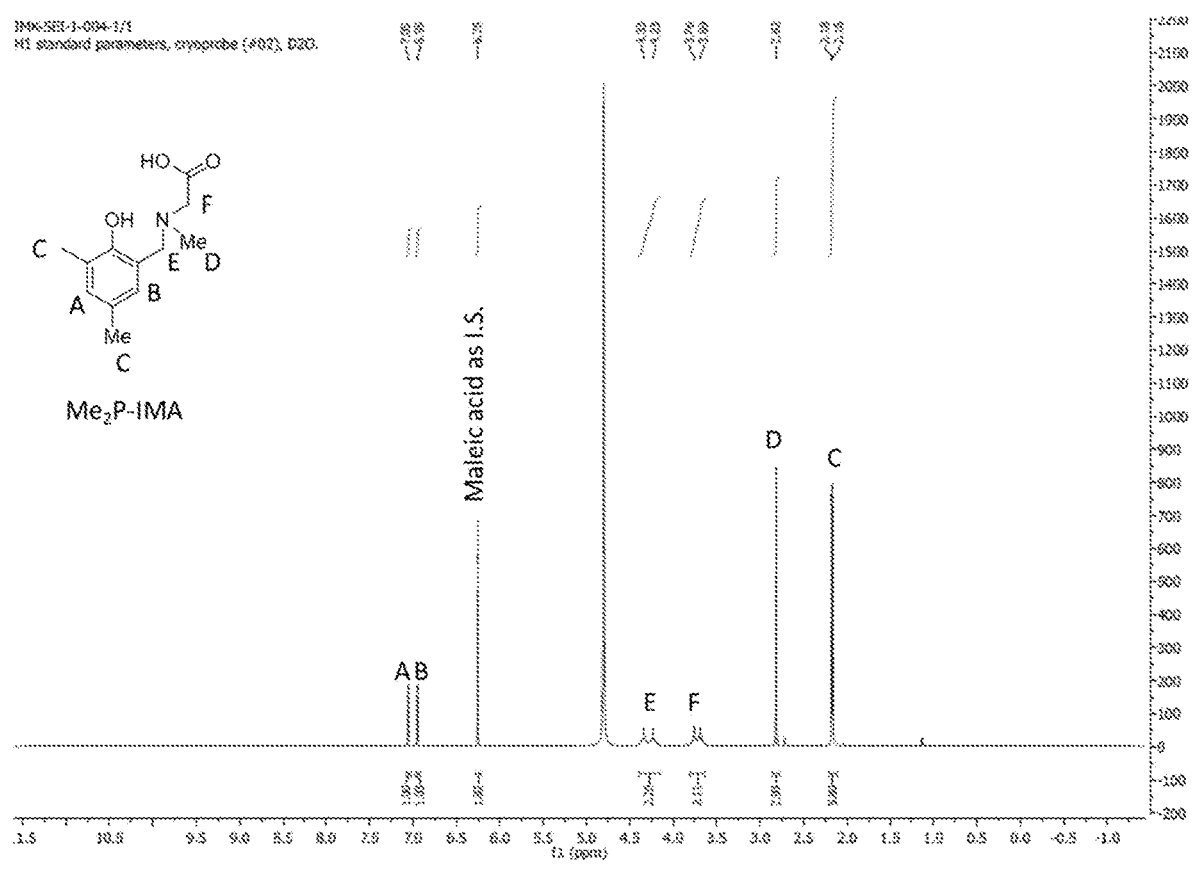

Figure 12. $^1$H-NMR of MP-IMA obtained from a reaction described in Example 6.
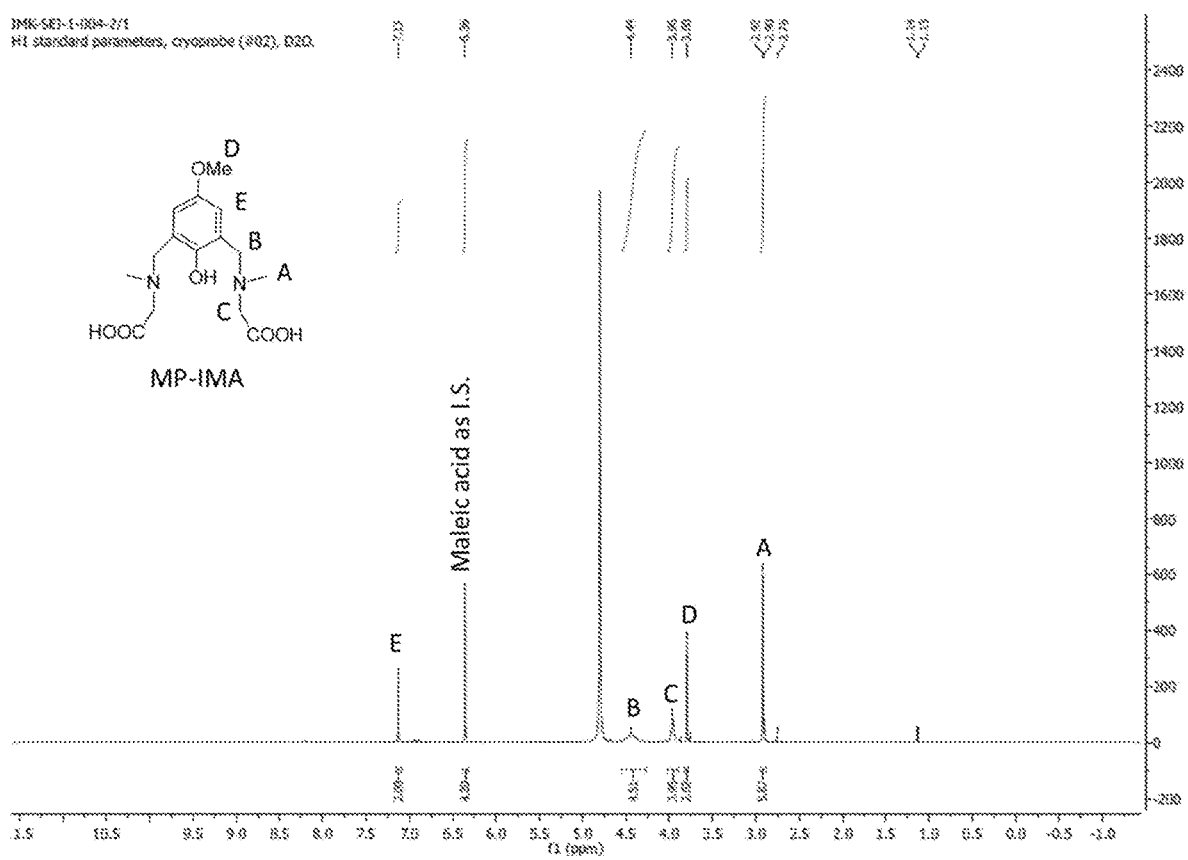

Figure 13. Comparison of bell pepper plants supplemented by DHE-IDA and Cres-IDA (right) and those with EDTA and EDDHA (left).
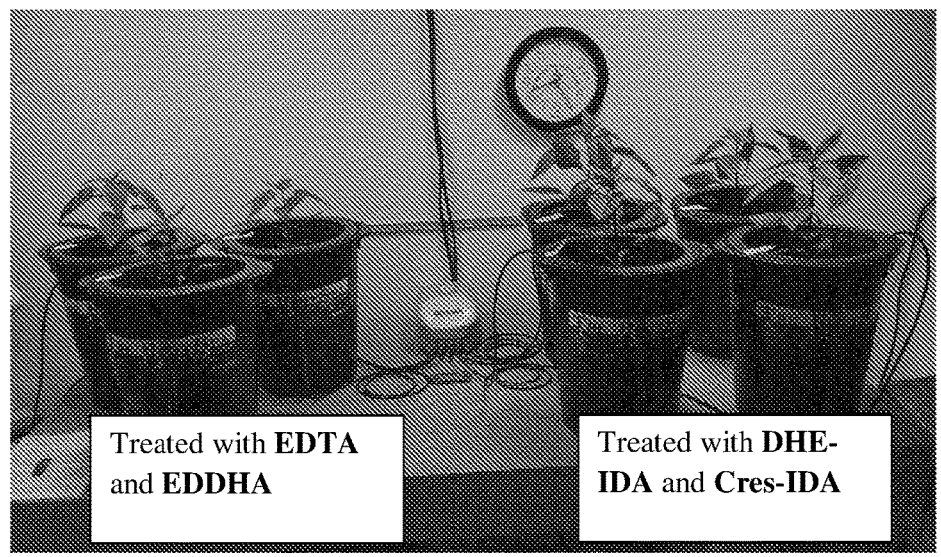

Figure 14. ¹H-NMR of PP-Sulf-Asp obtained from a reaction described in Example 5.
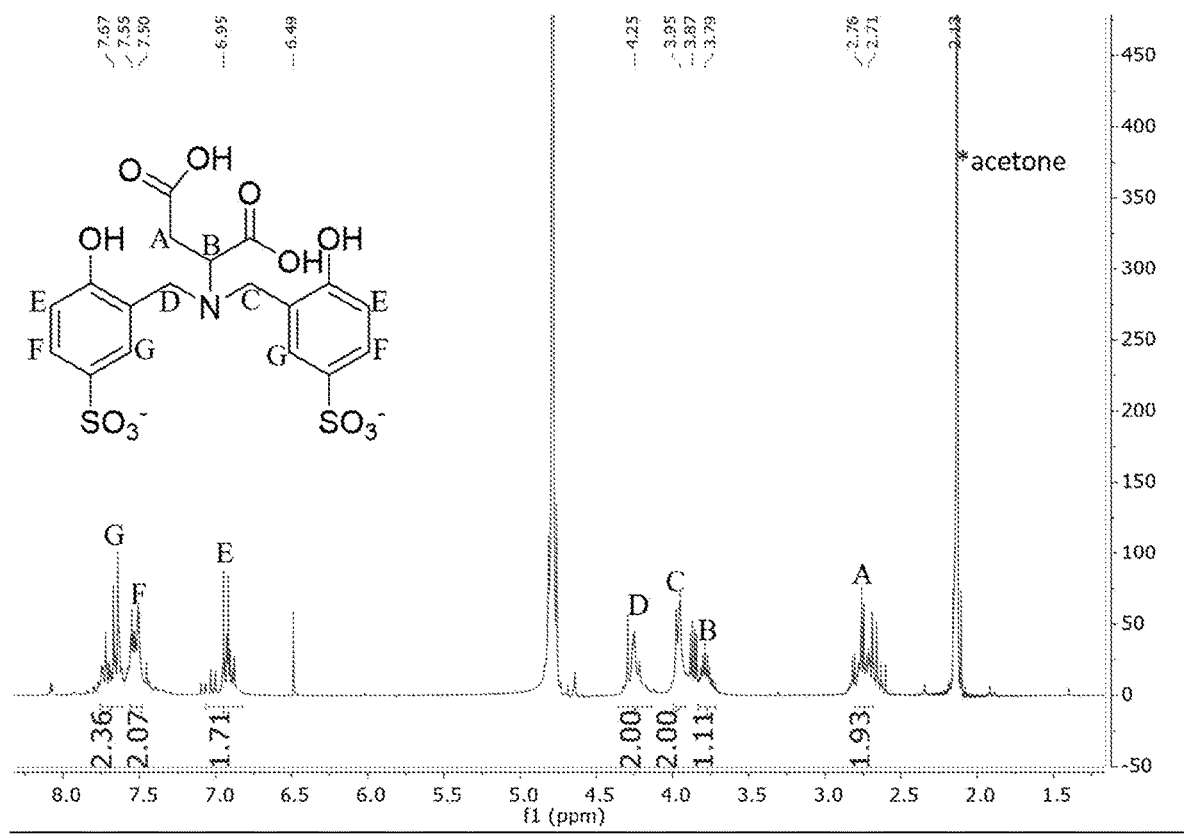

Figure 15. $^1$H-NMR of PP-Cres-Asp obtained from a reaction described in Example 5.
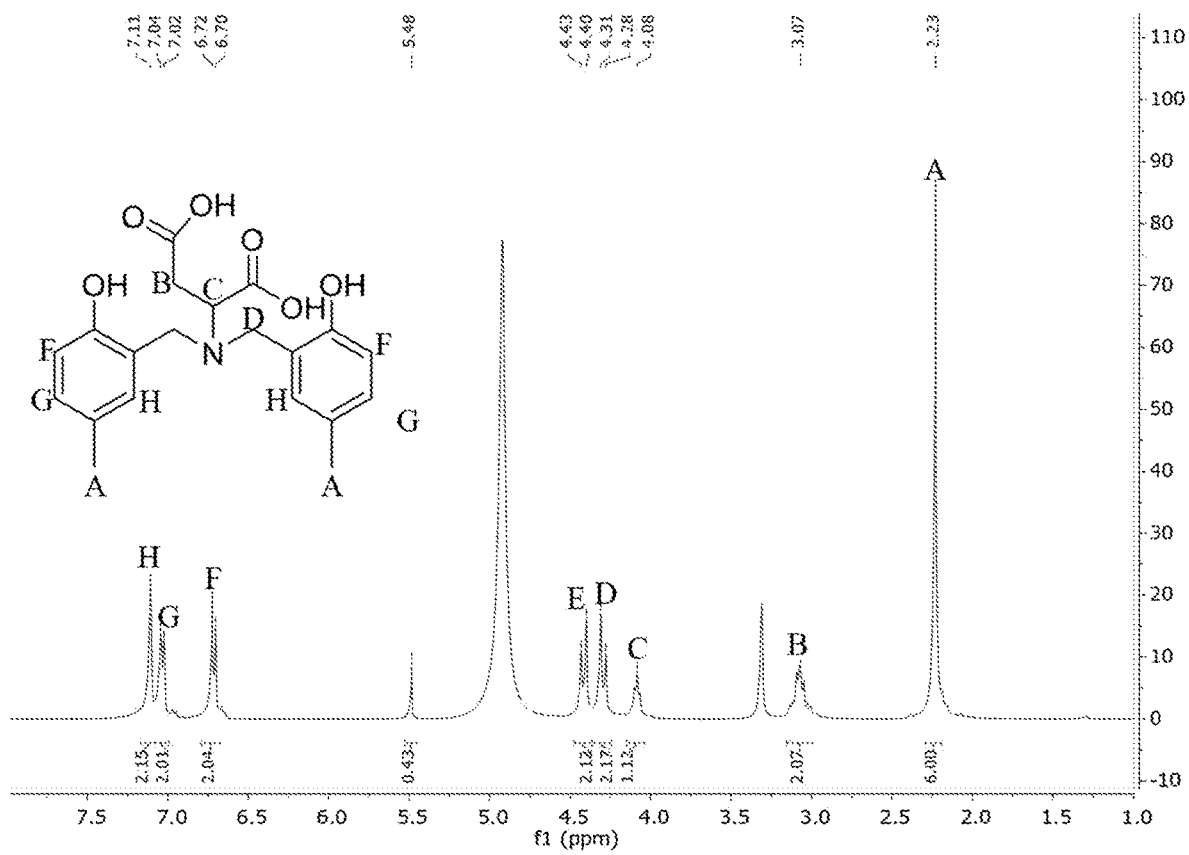

COMPOUNDS AND COMPOSITIONS FOR DELIVERY OF NUTRIENTS AND MICRONUTRIENTS TO PLANTS

CROSS-REFERENCE TO RELATED APPLICATIONS

The present application is a U.S. national stage of, and claims the priority benefit of, International Patent Application Serial No. PCT/US2016/039837, filed Jun. 28, 2016, and U.S. Provisional Application No. 62/186,206, filed Jun. 29, 2015, which are hereby incorporated herein in their entirety by reference.

Chelates are compounds that encapsulate metals and minerals. They have wide applications in cleaning detergents, pulp and paper industry, water treatment, agriculture, food preservation, chemical and oil processing, photography, and textiles. In agriculture, chelates are used to enhance the solubility and availability of nutrients and more particularly micronutrients such as iron. For example, iron deficiency in plants causes yellowing because iron is essential in production of chlorophyll. This condition is known as lime-induced chlorosis. It is most pronounced in basic soils where the pH is outside the window between pH 5 and 6.5. Most commonly used commercial chelates for fertilizer applications include ethylenediaminetetraacetic acid (EDTA), N-(hydroxyethyl)-ethylene diaminetriacetic acid (HEDTA), ethylene triaminepentaacetic acid (DTPA), and ethylenediamine-N,N'-bis(2-hydroxyphenylacetic acid (EDDHA). However, environmental impact from these reagents has necessitated the move towards more biologically friendly or biodegradable chelates such as ethylenediamine-N,N'-disuccinic acid (EDDS), amino acid chelates, amino sugars, and citrates. Poor binding and costs, however, have limited their use. The synthesis of several chelates for plant micronutrient application have been disclosed previously including N-substituted aspartic acids (U.S. Pat. No. 6,444,614), multi-dentate glycine containing chelating agents (U.S. Pat. No. 3,742,002), iminosuccinic acid (U.S. Pat. No. 6,870,026), amino acids, organic hydroxyacids and mixtures thereof (U.S. Pat. No. 5,504,055), benzoic acid derivatives (U.S. Pat. No. 8,137,429), arginine and glycine based nitrate amino acid chelates (WO 2009/089493), and aminocarboxylate catechols for cleaning applications (WO 2010/079409). However, these too have seen only limited use, presumably due to cost constraints. The present invention includes compounds and methods for delivering nutrients and micronutrients, such as iron, to plants where the compounds may be sourced from biomass.

SUMMARY OF THE INVENTION

In one aspect of the invention, compounds of Formula I are provided

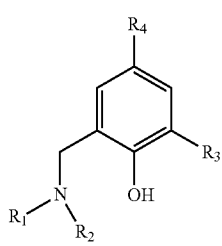

Formula I where $R_1$ is H, $C_1$-$C_4$ alkyl or $(CH_2)_n COOH$; $R_2$ is a $C_1$-$C_4$ alkyl, aryl, $(CH_2)_n COOH$, $(CH_2)_n CONH_2$, or $(CH_2)_n SR$; $R_3$ is $C_1$-$C_4$ alkyl, $CF_3$, $NO_2$, OR, X, or $(CH_2)_n NR_1 R_2$; $R_4$ is $C_1$-$C_4$ alkyl, $CF_3$, $NO_2$, OR, or X; n is 0, 1, 2, 3, or 4; R is H, $C_1$-$C_4$ alkyl or aryl; X is F, Br, Cl, or I.

In an additional aspect of the invention, compounds of Formula IIA and IIB are provided

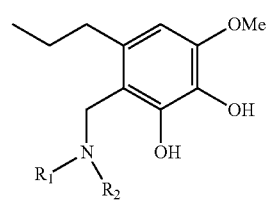

Formula IIA

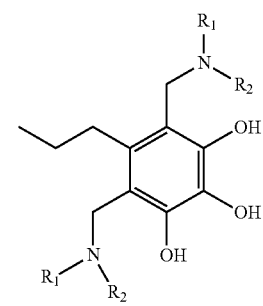

Formula IIB where $R_1$ is H, $C_1$-$C_4$ alkyl or $(CH_2)_n COOH$, and $R_2$ is a $C_1$-$C_4$ alkyl, aryl, $(CH_2)_n COOH$, $(CH_2)_n CONH_2$, or $(CH_2)_n SR$, where n is 0, 1, 2, 3, or 4 and R is H, $C_1$-$C_4$ alkyl or aryl.

Compounds of Formula IIIA and IIIB are further provided in additional aspects of the invention

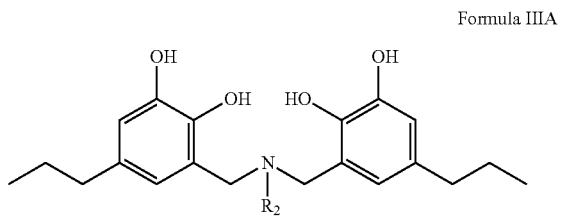

Formula IIIA

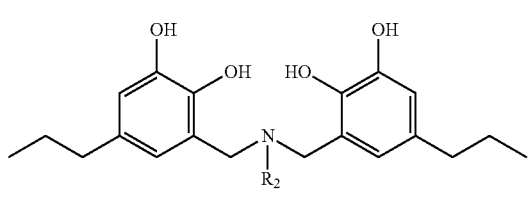

Formula IIIB where $R_2$ is H, $C_1$-$C_4$ alkyl, aryl, $(CH_2)_n COOH$, $(CH_2)_n CONH_2$, or $(CH_2)_n SR$ where n is 0, 1, 2, 3, or 4 and R is H, $C_1$-$C_4$ alkyl or aryl.

Compounds of Formula IV are also provided as further aspects of the invention

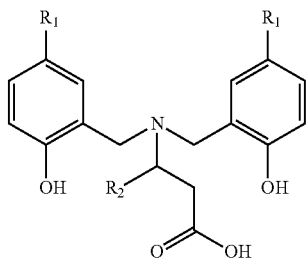

Formula IV where $R_1$ is $SO_3M$, COOM, or $C_1$-$C_4$ alkyl; $R_2$ is $CH_2COOH$, $CH_2OH$, $CHOHCH_3$, $CH_2SH$, $CH_2CH_2COOH$, or $CH_2CH_2SCH_3$; and M is an alkali metal.

In a further aspect of the invention, methods for preparing compounds of Formulae I, IIA, IIB, IIIA, IIIB, or IV are provided.

In still further aspects of the invention, methods for delivering nutrients or micronutrients to plants by administering one or more chelated compounds of Formulae I, IIA, IIB, IIIA, IIIB, or IV are provided.

In an additional aspect of the invention, methods for delivering nutrients or micronutrients to plants by administering one or compounds wherein at least one of the compounds is a secondary or tertiary amine substituted at the ortho position of a substituted phenol, wherein the phenol is further substituted at the other ortho position and optionally at the para position and wherein the compound is chelated to the nutrient or micronutrient and the nutrient or micronutrient is delivered to the plant.

In a further aspect of the invention, a composition comprising a chelated or unchelated compound of Formulae I, IIA, IIB, IIIA, IIIB, or IV is provided.

In an additional aspect of the invention, a method for delivering nutrients or micronutrients to plants of compounds of Formulae I, IIA, IIB, IIIA, IIIB, or IV are provided comprising administering to plants a composition comprising a chelated compound of Formulae I, IIA, IIB, IIIA, IIIB, or IV.

In a further aspect of the invention, a method for preventing lime-induced chlorosis in plants is provided comprising administering a compound of Formulae I, IIA, IIB, IIIA, IIIB, or IV chelated to a nutrient or micronutrient to a plant.

BRIEF DESCRIPTION OF THE DRAWINGS

FIG. 1 shows the structure of DHE-IA, DHE-IMA, and DHE-IDA.

FIG. 2 shows the structure of MPC-IA, MPC-IMA, MPC-IDA, PTP-IA, PTP-IMA, and PTD-IDA.

FIG. 3 shows the structure of DHE derivatives and OHP chelates.

FIG. 4 shows the structure of phenol-based imino acid chelates.

FIG. 5 shows the structure of para substituted phenol chelates.

FIG. 6 shows the structure of PP compounds.

FIG. 7 shows the $^1$H-NMR spectrum of DHE-IMA crude product obtained from Example 1.

FIG. 8 shows the $^1$H-NMR spectrum of DHE-IDA as set forth in Example 2.

FIG. 9 shows the $^1$H-NMR spectrum of Cres-IMA as set forth in Example 3.

FIG. 10 shows the $^1$H-NMR spectrum of Cres-IDA as set forth in Example 4.

FIG. 11 shows the $^1$H-NMR spectrum of $Me_2$P-IMA as set forth in Example 6.

FIG. 12 shows the $^1$H-NMR spectrum of MP-IMA as set forth in Example 6.

FIG. 13 is a comparison between DHE-IDA and Cres-IDA for delivering nutrients to bell pepper plants, with EDTA and EDDHA.

FIG. 14 is a $^1$H-NMR spectrum of PP-Sulf-Asp as set forth in Example 5.

FIG. 15 is a $^1$H-NMR spectrum of PP-Cre-Asp as set forth in Example 5.

DEFINITIONS

"Alkyl" refers to a straight-chain, branched or cyclic saturated aliphatic hydrocarbon. Typical alkyl groups include $C_1$-$C_4$ alkyls such as methyl, ethyl, propyl, isopropyl, butyl, isobutyl, tertiary butyl, and the like. The alkyl group may be optionally substituted with one or more substituents including, but not limited to, hydroxyl, amino, cyano, alkoxy, or one or more halogens.

"Aryl" refers to an aromatic group which has at least one ring having a conjugated pi electron system and includes carbocyclic aryl, heterocyclic aryl and biaryl groups. The aryl group may be optionally substituted with one or more substituents such as halogen, alkyl, hydroxyl, SH, OH, $NO_2$, amine, thioether, cyano, alkoxy, and amino. Examples of aryl groups include phenyl, napthyl and anthracyl groups.

Those of ordinary skill in the art will appreciate that when referencing a substituent herein such as "$CH_2COOH$", for example, the point of attachment is where valency would ordinarily permit. Thus, in this example, such attachment would be at the methylene carbon.

DETAILED DESCRIPTION OF THE INVENTION

An example of a molecule that may be prepared from lignin in biomass is 2-methoxy-4-propylphenol also known as dihydroeugenol or DHE. A preparation of DHE from lignin in biomass is described in WO/2015/061802 which is incorporated herein by reference. DHE is also commercially available. Another example of a biomass/lignin derived compound used herein is 2,6-dimethoxy-4-propylphenol also known as propylsyringol or DMPP. A preparation of DMPP from lignin in biomass is described in (WO 2015/061802). DMPP may also be obtained commercially. DHE and DMPP may be modified as set forth herein to create compounds with multi-dentate chelating ligands that may be used to deliver nutrients and micronutrients (such as iron) to plants.

For example, compounds of Formulae I, IIA, IIB, IIIA, IIIB, or IV may be prepared from lignin or other biomass. By using lignin, for instance, valuable compounds may be obtained from biomass that would otherwise be discarded. Such compounds may be prepared, for example, by the base-catalyzed condensation of DHE, DMPP or other phenolic derivatives with organic amines including amino acids or amino alcohols. Examples of such amines include, for example, IA, IMA, or IDA. The condensation further takes place in the presence of formaldeyde (37% or 50% solutions for instance) under reflux or under ambient conditions in a water-alcohol solvent (where the alcohol is methanol, ethanol, propanol, iso-propanol, butanol, ethylene or propylene glycol) or neat medium without added solvent. Neutralization of the reaction mixture with an acid, such as hydrochloric acid, followed by solvent evaporation provides the chelate structure in high yield and good purity. Removal or concentration of solvent to a desired volume can provide a concentrated solution of said chelate for various applications without need for complete separation. Post separation crystallization can provide a chelate in high analytical purity. Standard methods known in the art may be used to chelate a metal such as iron, for example, to the compounds of Formulae I, IIA, IIB, IIIA, IIIB, or IV.

A patent for the preparation of p-cresol iminodiacetic acid (Cres-IDA) was assigned to Ciba Geigy (patent no. CH288380 (A), 1953). Yet another embodiment of this invention includes the preparation of analogous chelates via condensation of other phenolic precursors such as p-methoxyphenol (MP), 2,4-dimethylphenol (Me$_2$P), 2-methoxy-p-cresol (MoCres), 2-tBu-p-methoxyphenol (tBuMP) and 4-ethyl phenol (EP) (FIG. 4) with aqueous formaldehyde and the said iminoacetic acids. Among these chelates, the processes for MP-IMA, Me$_2$-PIMA, MoCres-IMA and tBuMP-IMA synthesis from their respective phenols and sarcosine have been disclosed in the literature (G. J. Wilson, Australian Journal of Chemistry, 1990), 43, 783-789). However, their use and application in delivery of micronutrients for agricultural applications and as nutrient enhancers has not been previously disclosed.

With respect to compounds of Formula I, in some embodiments of the invention, $R_1$ is H, methyl or $(CH_2)_n COOH$ with n being 0, 1, 2, 3, or 4 and $R_2$ is $(CH_2)_n COOH$. In these and other embodiments, $R_1$ is methyl and $R_2$ is $(CH_2)_n COOH$ with n being 0, 1, 2, 3, or 4. In a typical embodiment n is 1.

In these and other embodiments, $R_3$ is $C_1$-$C_4$ alkyl, OR, or $(CH_2)NR_1R_2$; $R_1$ is H, $C_1$-$C_4$ alkyl or $(CH_2)_n COOH$; $R_2$ is $C_1$-$C_4$ alkyl, aryl, $(CH_2)_n COOH$, $(CH_2)_n CONH_2$, or $(CH_2)_n SR$; R is H, $C_1$-$C_4$ alkyl or aryl; and n is 0, 1, 2, 3, or 4. Often, n is 1 in such embodiments. Such embodiments include compounds where $R_3$ is O—CH$_3$, t-butyl or $(CH_2)NR_1R_2$ where $R_1$ is H, methyl, or $(CH_2)COOH$. Embodiments of compounds of Formula 1 include where $R_4$ is $C_1$-$C_4$ alkyl or OR such as methyl, propyl, or O—CH$_3$.

Examples of structures of Formula I include:

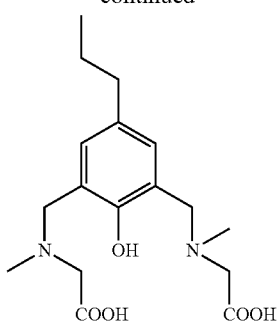
Cres-IMA

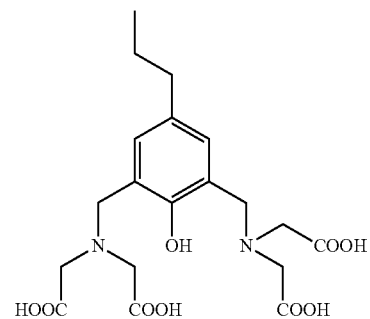
Cres-IDA

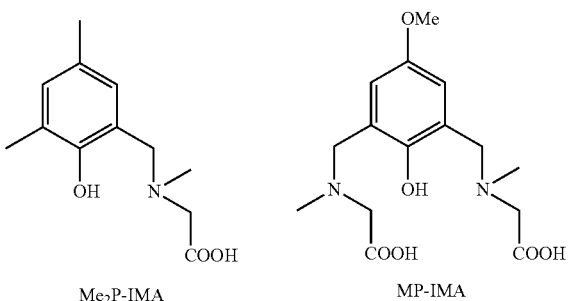
Me$_2$P-IMA          MP-IMA

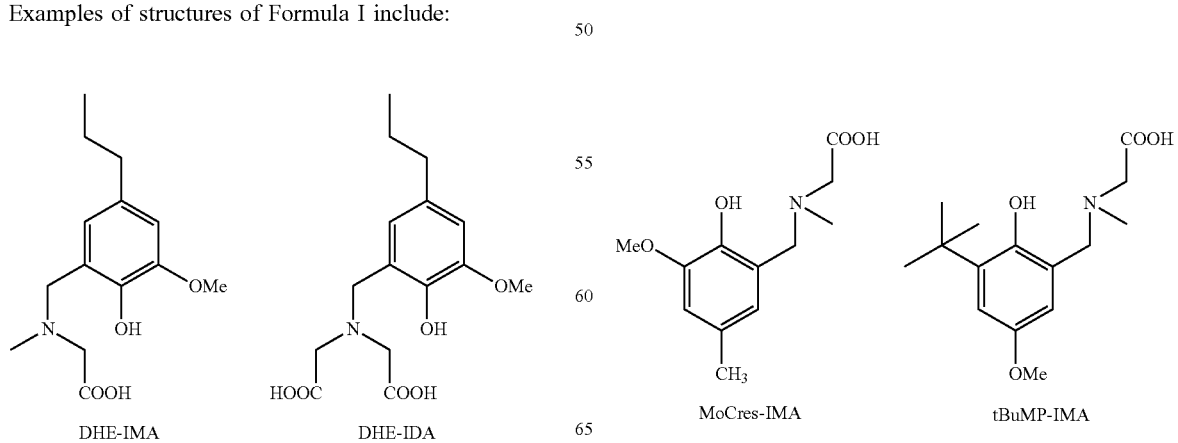
DHE-IMA    DHE-IDA    MoCres-IMA    tBuMP-IMA

Additional compounds of Formula I include compounds of Formula IA:

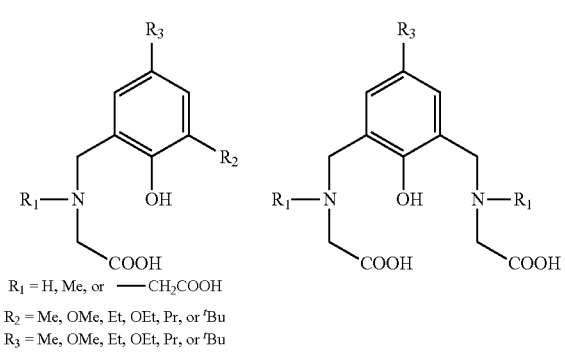

Formula IA $R_1$ = H, Me, or —CH$_2$COOH
$R_2$ = Me, OMe, Et, OEt, Pr, or $^t$Bu
$R_3$ = Me, OMe, Et, OEt, Pr, or $^t$Bu The compounds of Formula I may be chelated to one or more nutrients or micronutrients such as a metal such as iron, zinc, managenes or copper with iron being a typical metal for chelation as a micronutrient.

A preparation of DHE-IMA is set forth in Example 1. A preparation of DHE-IDA is set forth in Example 2. A larger-scale preparation of DHE-IDA is exemplified in Example 2A and a Cres-IDA preparation is exemplified in Example 4 with a larger-scale batch in Example 4A. Preparations for MP-IMA, Me$_2$P-IMA, MoCres-IMA, and tBuMP-IMA are all set forth in Example 6.

Compounds of Formulae IIA and IIB may be prepared by base catalyzed condensation of biomass derived DHE or DMPP-derivatives (MPC and PTP) with iminoacetic acids (glycine (IA), sarcosine (IMA), or iminodiacetic acid (IDA)) and aqueous formaldehyde. The structures of MPC and PTP are set forth below:

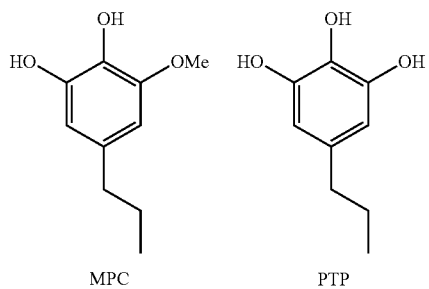

MPC   PTP and their preparation has been previously reported in Shou Zhao and Mahdi M. Abu-Omar, "Biobased Epoxy Nanocomposites Derived from Lignin-Based Monomers," *Biomacromolecules*, 2015, 16, 2025-2031.

With respect to compounds of Formula IIA and IIB, embodiments include where $R_1$ is H, methyl or $(CH_2)_n$COOH and $R_2$ is $(CH_2)_n$COOH, and n is 0, 1, 2, 3, or 4. In a typical embodiment, n is 1. Examples of compounds falling within the scope of Formula IIA or IIB include MPC-IA, MPC-IMA, MPC-IDA, PTP-IA, PTP-IMA, and PTP-IDA.

Compounds of Formulae IIIA and IIIB which are based on catechol derivatives of DHE and ortho-hydroxyphenols (abbreviated OHP, FIG. 3) can likewise be prepared via condensation of OHP with aqueous formaldehyde and organic amines.

With respect to compounds of Formula IIIA and IIIB, embodiments include where $R_2$ is $(CH_2)_n$COOH and n is 1.

Compounds of Formula IV which are based on para-substituted phenols (abbreviated PP, FIG. 5) can be prepared via condensation of PP with aqueous formaldehyde and amino acid derivatives. The resulting products include but are not limited to PP-Sulf-Asp and P-Cres-Asp (FIG. 6).

With respect to compound of Formula IV, embodiments include where $R_1$ is SO$_3$M, and $R_2$ is CH$_2$COOH. Examples of compounds of Formula IV include:

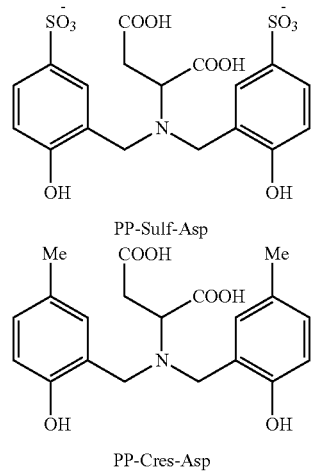

PP-Sulf-Asp

PP-Cres-Asp

In many embodiments, M is potassium. In other embodiments of Formula IV, $R_1$ is methyl and $R_2$ is CH$_2$COOH. Examples of Formula IV compounds include PP-Sulf-Asp and PP-Cres-Asp.

All plants and vegetables require iron so the methods of the invention may be applied broadly. For example, the method may be applied to deliver iron to the *Calibrachoa*, *Petunia*, or *Capsiucum* genuses. Further embodiments of the invention include methods of delivering a nutrient to a plant comprising administering a compound of Formula I, IIA, IIB, IIIA, IIIB, or IV wherein such compound is chelated to one or more nutrients such as a metal with a typical metal being iron. Such methods may be used, for example, to prevent lime-induced chlorosis. When the methods of the invention are used to deliver, for example, iron to plants, the amount of iron delivered may be measured. For example, such values include between about 50 ppm and about 150 ppm including all values in between. Such values further include between about 50 ppm to 80 ppm, 60 ppm to 80 ppm, 70 ppm to 80 ppm and about 80 ppm itself. Other values include between about 80 ppm and about 150 and all values in between including between about 100 ppm and 150 ppm, 110 ppm and 150 ppm, 120 ppm and 150 ppm, 130 ppm and 145 ppm, 135 ppm and 145 ppm, including about 136 ppm, 137 ppm, 138 ppm, 139 ppm, 140 ppm, 141 ppm, 142 ppm, 143 ppm, 144 ppm, and 145 ppm, and values greater than about 150 ppm. As used herein, the term "about" is in reference to measurement error used to measure iron content by elemental analysis as set forth herein.

Additional embodiments of the invention include delivering nutrients or micronutrients such as a metal, with a typical metal being iron, by administering a composition comprising a compound of Formulae I, IIA, IIB, IIIA, IIIB, or IV so chelated to the nutrient or micronutrient. The composition may further comprise an excipient. Excipients may be, for example, anti-foaming agents or bulking agents or preservatives such as propyl paraben. Further embodiments of the invention include methods for delivering nutrients or micronutrients, such as one or more metals, with a typical metal being iron, to plants by administering one or compounds wherein at least one of the compounds is a secondary or tertiary amine substituted at the ortho position of a substituted phenol, wherein the phenol is further substituted at the other ortho position and optionally at the para position and wherein the compound is chelated to the nutrient or micronutrient and the nutrient or micronutrient is delivered to the plant.

In Example 7, DHE-IDA and Cres-IDA were chelated with iron and used to deliver iron micronutrients to the *Capsicum annum* species of bell pepper plants. As disclosed in Example 7, the amount of iron delivered was substantially greater than EDTA or EDDHA chelates. When looking at plant growth, DHE-IDA supplemented Steiner hydroponic solution was comparable to controls using conventional EDTA or EDDHA and superior to plants where only iron salts without chelate were used. Plant tissue analyses further confirmed higher iron content in bell pepper plants receiving a 4 ppm iron-DHE-IDA complex.

The use of PP derived chelates such as PP-Sulf-Asp and PP-cres-Asp to deliver micronutrient iron to *Calibrachoa* and *Petunia* plants was demonstrated under environmentally controlled (temperature and lighting) conditions in a greenhouse. Plant growth with PP-Cres-Asp chelated iron was superior to controls using EDTA chelated iron and superior to plants where only iron salt without chelate was used. Plant tissue analysis confirmed higher iron content in plants receiving 4 ppm iron-PP-Cres complex.

EXAMPLES

The process for the preparation of the aforementioned chelating agents is exemplified below.

Example 1. Preparation of DHE-IMA

DHE-IMA was prepared by base catalyzed condensation of commercially available DHE, sarcosine and formaldehyde. In this process, DHE (20 mmol), sarcosine (22 mmol), 37% formaldehyde solution (22 mmol) and solid NaOH (20 mmol) were added in 40 mL water-ethanol (1:2 v/v) in a 100 mL round bottom flask. The mixture was heated with continuous stirring to dissolve sarcosine and NaOH, and then refluxed at 90° C. for 11 h. The color of the solution gradually changed to light brown as the reaction progressed. After 11 h of reflux, the solution was cooled down to room temperature by removing the heat source and neutralized by drop wise addition of 3 M HCl. The crude product was obtained after evaporating solvent by using a rotary evaporator and then drying it in air. This product was further washed with hexane, filtered and dried in air to obtain DHEIMA (white powder) with 97% yield (4.9 g). The purity of DHEIMA was confirmed by $^1$H-NMR (FIG. 7). $^1$H-HMR (400 MHz, DMSO-$d_6$): δ (ppm) 6.74 (s, 1H), 6.62 (s, 1H), 3.96 (s, 3H), 3.74 (s, 3H), 3.28 (s, 2H), 2.53 (s, 2H), 2.43 (s, 2H), 1.54 (q, 2H), 0.85 (t, 3H).

Example 2: Preparation of DHE-IDA

DHE-IDA was prepared by a base catalyzed condensation of commercially available DHE, iminodiacetic acid (IDA) and formaldehyde. DHE (20 mmol), 37% formaldehyde solution (22 mmol), IDA (22 mmol) and 2 molar equivalent of NaOH were added in 40 mL water-ethanol solvent (1:2 v/v) in a 100 mL round bottom flask. The mixture was heated with continuous stirring to dissolve IDA and NaOH, and then refluxed at 90° C. for 11 h. The color of the reaction mixture initially changed to light purple within 30 minutes, and then gradually changed to light brownish as the reaction progressed. After about 6 h of reflux, the reaction mixture became colloidal as white solid started to form. After refluxing for another 3 h, the solution became thick with white solid which was cooled down to room temperature, neutralized with 3 M HCl and kept in a refrigerator for about 2 h. White product was filtered, washed and dried in an oven at 50° C. to obtain DHEIDA with 95% yield (5.6 g). The purity of the product was confirmed by $^1$H-NMR (FIG. 8). $^1$H-HMR (400 MHz, DMSO-$d_6$): δ (ppm) 6.89 (s, 1H), 6.66 (s, 1H), 4.03 (s, 3H), 3.61 (s, 4H), 3.41 (s, 4H), 2.43 (t, 2H), 1.55 (q, 2H), 0.83 (t, 3H).

Example 2A: Preparation of DHE-IDA in a Larger Batch

In this batch, the process for the preparation of DHEIDA, as described in Example 2, was scaled by 2× times by following the similar methodology described thereof. Total yield of DHEIDA was 96% (12 g).

Example 3. Preparation of Cres-IMA

Cres-IMA was prepared by a base catalyzed condensation of commercially available p-cresol, sarcosine and formaldehyde. p-Cresol (46 mmol), sarcosine (101 mmol), 37% formaldehyde solution (92 mmol) and solid NaOH (100 mmol) were added in 100 mL water-ethanol (1:2 v/v) solvent in a 250 mL round bottom flask. The mixture was heated with continuous stirring to dissolve p-cresol, sarcosine and NaOH, and then refluxed at 90° C. for 11 h. The color of the solution gradually changed to light brownish as the reaction progressed. After 11 h of reflux, the solution was cooled down to room temperature by removing the heat source and neutralized by drop wise addition of 3 M HCl, and further cooled down by keeping the solution in a refrigerator. The crude light brownish oily product was obtained after removing solvent by using a rotary evaporator. The purity of the product was analyzed $^1$H-NMR (FIG. 9). $^1$H HMR (400 MHz, $D_2O$): δ (ppm) 6.97 (s, 2H), 3.92 (s, 4H), 3.39 (s, 4H), 2.48 (s, 6H), 2.14 (S, 3H).

Example 4. Preparation of Cres-IDA

Cres-IDA was prepared by a base catalyzed condensation of commercially available p-cresol, IDA and formaldehyde. p-Cresol (9 mmol), IDA (20 mmol), 37% formaldehyde solution (20 mmol) and NaOH (40 mmol) were added in 20 mL water-ethanol (1:2 v/v) solvent in a 100 mL round bottom flask. The mixture was heated with continuous stirring to dissolve p-cresol, IDA and NaOH, and then refluxed at 90° C. for 11 h. After 11 h of reflux, the solution was cooled down to room temperature by removing the heat source and neutralized by drop wise addition of 3(M) HCl. The solution was further cooled down in a refrigerator. Solvent was removed by using a rotary evaporator to obtain light brownish oily product (3.2 g, 90% yield). White solid was formed when a small amount of this oily product was partially dissolved in butanol and hexane mixture and kept the vial containing the solution at room temperature for 2 days. White solid was filtered, washed with hexane and died in air. The purity of the oily product was analyzed by $^1$H NMR (FIG. 10). $^1$H HMR (400 MHz, D$_2$O): δ (ppm) 7.03 (s, 2H), 6.66 (s, 1H), 4.03 (s, 4H), 3.46 (s, 4H), 2.20 (s, 3H).

Example 4A. Preparation of Cres-IDA in a Larger Batch

In this reaction, the process for the preparation of Cres-IDA, as described in Example 4, was scaled by 5.5 times by following the similar methodology described thereof. Total yield of Cres-IDA as oily liquid was 18.9 g (94%).

Example 5. Preparation of PP-Sulf-Asp and PP-Cres-Asp

These chelating agents were prepared by a base catalyzed (KOH) condensation of their respective para-substituted phenol precursors (p-cresol (Cres), 4-hydroxybenzenesulfonic acid (Sulf), aspartic acid, and 37% aqueous formaldehyde solution (all commercially available). For the synthesis of PP-Sulf-Asp, 1 molar equivalent of aspartic acid, 2 molar equivalents formaldehyde, and 2 molar equivalents KOH were dissolved in a small amount of water and added to an aqueous solution of 1 molar equivalent Sulf. For the synthesis of PP-Cres-Asp, 1 molar equivalent of aspartic acid, 2 molar equivalents formaldehyde, and 2 molar equivalents KOH were dissolved in small amount of water and added to a solution of 1 molar equivalent Cres dissolved in water-methanol (1:2 v/v) solvent. The resulting mixtures were refluxed at 90° C. for 11 hr. After 11 of reflux, the solution was cooled to room temperature, and solvent removed by roto-evaporation to yield a solid product. The purity of the PP-Sulf-Asp and PP-Cres-Asp chelating agents were analyzed by $^1$H-NMR. $^1$H-NMR of PP-Cres-Asp (FIG. 15) (400 MHz, D$_2$O): δ (ppm) 2.23 (s, 6H), 3.07 (m, 2H), 4.08 (t, H), 4.28 (dd, 2H), 4.40 (dd, 2H), 6.7 (d, 2H), 7.02 (d, 2H), 7.1 (s, 2H). $^1$H-NMR of PP-Sulf-Asp (FIG. 14) (400 MHz, D$_2$O): δ (ppm) 2.76 (m, 2H), 3.79 (m, H), 3.95 (m, 2H), 4.25 (m, 2H), 6.95 (m, 2H), 7.5 (m, 2H), 7.67 (m, 2H).

Example 6. Preparation of MP-IMA, Me$_2$P-IMA, MoCres-IMA and tBuMP-IMA

These chelating agents were prepared by a base catalyzed (NaOH) condensation of their respective phenol precursors (p-methoxyphenol (MP), 2,4-dimethylphenol (Me$_2$P), 2-methoxy-p-cresol (MoCres), 2-tBu-p-methoxyphenol (tBuMP) and 4-ethyl phenol (EP)), sarcosine and 37% aqueous formaldehyde solution in 20-30 mL iPrOH in a 100 mL round bottom flask. For the synthesis of MPIMA, 2 molar equivalents of sarcosine and NaOH, based on the amount of phenol precursor, were used, whereas for Me$_2$PIMA, MoCresIMA and tBuMPIMA, 1 molar equivalent of sarcosine and NaOH were added. Small amount of water (1-5 mL) was also added to dissolve sarcosine and NaOH. The mixture was refluxed with continuous stirring at 80-85° C. for 7-8 h and the crude products were recovered by following the similar methodology described in Example 3. The purity of Me$_2$P-IMA and MP-IMA were checked by $^1$H-NMR (FIGS. 11-12). $^1$H HMR for Me$_2$P-IMA (400 MHz, D$_2$O): δ (ppm) 7.05 (s, 1H), 6.95 (s, 1H), 4.33 (d, 2H), 3.76 (d, 2H), 2.82 (s, 3H), 2.18 (s, 6H). $^1$H-HMR for MP-IMA (400 MHz, D$_2$O): δ (ppm) 7.13 (s, 2H), 4.44 (s, 4H), 3.96 (s, 4H), 3.80 (s, 3H), 2.90 (s, 6H).

Example 7. Use of DHE-IDA and Cres-IDA as Chelates for Iron Micronutrient

Seven (7) identical cultivated varieties of bell pepper plants, *Capsicum annuum* were grown in individual five-gallon containers deep-water-culture (DWC) containers (the Root Spa bucket system by Hydrofarm) that is continuously aerated by a single oxygen line that stems from an air pump in a soilless media of rockwool surrounded by clay pebbles in a mesh tray that rests on top of the buckets. The pepper plants were grown indoors with an ambient air temperature of around 72° F. The light source came from high-pressure sodium bulbs with a light interval of 12 hours on and 12 hours off.

The pepper plants were grown with a beginning identical nutritional mix similar to that of a Steiner hydroponic solution. Once all 7 pepper plants grew to a size that allowed them to be fertilized at full strength, the Steiner solution was replaced with a different Steiner solution that does not have any iron. The total solution pH was raised to 8 and adjusted daily to maintain the pH at 8. Potassium hydroxide was used to increase the pH. There were 7 treatments of iron added (or not added) to each bucket as follows:

Treatment 1: Control (no iron)
Treatment 2: 4 ppm DHE-IDA Fe chelate
Treatment 3: 4 ppm Cres-IDA Fe chelate
Treatment 4: 4 ppm Fe EDTA
Treatment 5: 4 ppm Fe EDDHA
Treatment 6: 4 ppm iron sulfate; 4 ppm DHE-IDA chelate
Treatment 7: 4 ppm iron sulfate; 8 ppm Cres-IDA chelate As more water was needed, the appropriate amount of no-iron Steiner solution and Fe-chelate/Fe-chelate mixture was added to maintain a finished iron solution of 4 ppm.

Leaf samples (at least two per plant) were collected at the end of the normal nutritional program (2 weeks). The overall growth of the plants in Treatments 2, 3, 6, and 7 were comparable and at least level if not better with Treatments 4 and 5 (FIG. 13). This result demonstrates the ability of DHE-IDA and Cres-IDA to maintain sufficient soluble iron for normal plant growth as well as their utility as nutrient enhancers added separately from the metal salts as in Treatments 6 and 7. Elemental analyses of iron content in the plants leaves was carried out after week 2. Iron content in plant leaves from Treatments 2, 3, 6, and 7 were comparable at 143 ppm iron. Iron content in Treatment 5 was 91 ppm and Treatment 4 134 ppm.

Example 8. Use of PP-Derived Chelates for Iron Micronutrient

In order to establish the efficacy of PP-derived chelates, we applied the PP-Cres-Asp iron chelate to two plant species known in the field to have difficulties in absorbing iron, *Calibrachoa* and *Petunia* plants. In this trial, the plants were grown in soilless media (80% peat and 20% perlite) with lime to increase the target pH to 7.0, a pH that is averse to iron uptake in plants. All plants were top dressed with a standard polymer-coated fertilizer to provide the standard nitrogen, phosphorus, and potassium nutrition along with other micro nutrients, excluding iron. Lighting was controlled for 16-hour days. There were 3 treatments of iron added (or not added) to each bucket as follows:

Treatment 1: 4 ppm unchelated Fe
Treatment 2: 4 ppm Fe EDTA
Treatment 3: 4 ppm PP-Cres-Asp Treatments 1-3 were applied to the respective plants as a drench for 3 weeks. Following 3 weeks of treatment, tissue samples were gathered from each plant and subjected to elemental analysis for measurement of iron content in the plant tissue. Elemental analysis of the plant tissue from *Calibrachoa* plants was found to contain 30 ppm Fe in plants receiving Treatment 1, 39 ppm Fe in plants receiving Treatment 2, and 56 ppm Fe in plants receiving Treatment 3. Elemental analysis of the plant tissue from *Petunia* plants was found to contain 43 ppm Fe in plants receiving Treatment 1, 45 ppm Fe in plants receiving Treatment 2, and 80 ppm Fe in plants receiving Treatment 3. These elemental analysis results show the there is a significant improvement in iron uptake by plants treated with PP-Cres-Asp chelated Fe than plants treated with EDDTA chelated Fe under the conditions studied.

What is claimed is:

1. A compound of Formula I:

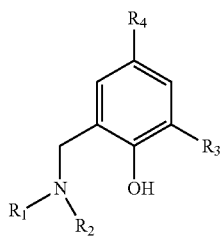

Formula I wherein $R_1$ is a methyl group; $R_2$ is $(CH_2)_nCOOH$; $R_3$ is selected from the group consisting of $C_1$-$C_4$ alkyl groups, $CF_3$, $NO_2$, OR, X, and $(CH_2)_nNR_1R_2$; $R_4$ is selected from the group consisting of $C_1$-$C_4$ alkyl groups, $CF_3$, $NO_2$, OR, and X; wherein n is 0, 1, 2, 3, or 4; wherein R is selected from the group consisting of H, $C_1$-$C_4$ alkyl groups and aryl groups; and wherein X is selected from the group consisting of F, Br, Cl, and I.

2. The compound according to claim 1, wherein $R_2$ is $(CH_2)_nCOOH$ and wherein n is 1.

3. The compound of claim 1, wherein $R_3$ is selected from the group consisting of $C_1$-$C_4$ alkyl groups, OR, wherein R is selected from the group consisting of H, $C_1$-$C_4$ alkyl groups and aryl groups, and $(CH_2)_nNR_1R_2$.

4. The compound of claim 1 wherein $R_3$ is selected from the group consisting of O-Me, t-butyl, and $(CH_2)NR_1R_2$ groups.

5. The compound of claim 3, wherein $R_3$ is $(CH_2)_nNR_1R_2$ and wherein n is 1.

6. The compound of claim 1, wherein $R_4$ is selected from the group consisting of $C_1$-$C_4$ alkyl groups and OR.

7. The compound of claim 1, wherein $R_4$ is selected from the group consisting of methyl, propyl, and O-methyl groups.

8. The compound of claim 1 having the formula:

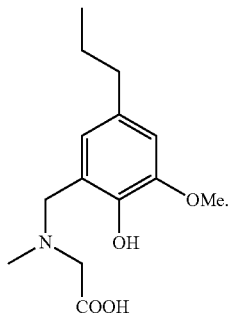 [SMILES: CCCc1cc(CN(C)CC(=O)O)c(O)c(OC)c1]

9. The compound of claim 1, wherein said compound is chelated to a nutrient or micronutrient.

10. The compound of claim 9, wherein said nutrient or micronutrient is a metal.

11. The compound of claim 10, wherein said compound is chelated to iron, zinc, manganese or copper.

12. The compound of claim 2, wherein said compound is chelated to a nutrient or micronutrient.

13. The compound of claim 12, wherein said nutrient or micronutrient is a metal.

14. The compound claim 13, wherein said compound is chelated to iron, zinc, manganese or copper.

15. The compound of claim 4, wherein said compound is chelated to a nutrient or micronutrient.

16. The compound of claim 15, wherein said nutrient or micronutrient is a metal.

17. The compound of claim 16, wherein said compound is chelated to iron, zinc, manganese or copper.

18. The compound of claim 5, wherein said compound is chelated to a nutrient or micronutrient.

19. The compound of claim 18, wherein said nutrient or micronutrient is a metal.

20. The compound of claim 19, wherein said compound is chelated to iron, zinc, manganese or copper.

21. The compound of claim 6, wherein said compound is chelated to a nutrient or micronutrient.

22. The compound of claim 21, wherein said nutrient or micronutrient is a metal.

23. The compound of claim 22, wherein said compound is chelated to iron, zinc, manganese or copper.

24. The compound of claim 7, wherein said compound is chelated to a nutrient or micronutrient.

25. The compound of claim 24, wherein said nutrient or micronutrient is a metal.

26. The compound of claim 25, wherein said compound is chelated to iron, zinc, manganese or copper.

27. The compound of claim 8, wherein said compound is chelated to a nutrient or micronutrient.

28. The compound of claim 27, wherein said nutrient or micronutrient is a metal.

29. The compound of claim 28, wherein said compound is chelated to iron, zinc, manganese or copper.

* * * * *